United States Patent [19]

Hahn

[11] Patent Number: 4,694,141

[45] Date of Patent: Sep. 15, 1987

[54] AUTOMATIC WELDER'S HELMET

[75] Inventor: Lawrence R. Hahn, Pickens, S.C.

[73] Assignee: The Fourth Dimension, Inc., Pickens, S.C.

[21] Appl. No.: 925,156

[22] Filed: Oct. 31, 1986

[51] Int. Cl.$^4$ ............................ A23K 9/32; A61F 9/06
[52] U.S. Cl. .......................................... 219/147; 2/8; 2/436
[58] Field of Search ................. 2/8, 11, 206, 427, 436; 219/147

[56] References Cited

U.S. PATENT DOCUMENTS

| | | | |
|---|---|---|---|
| 2,354,502 | 7/1944 | Cockrill et al. | 2/8 |
| 3,096,430 | 7/1963 | Farr | 219/147 |
| 3,692,974 | 9/1972 | Thomason et al. | 219/147 |
| 3,838,247 | 9/1974 | Finger et al. | 219/147 |
| 3,943,573 | 3/1976 | Budmiger | 2/8 |
| 4,293,757 | 10/1981 | Niemi | 219/147 |
| 4,418,267 | 11/1983 | Pfanzelt | 219/147 |

FOREIGN PATENT DOCUMENTS

| | | | |
|---|---|---|---|
| 499229 | 11/1954 | Italy | 219/147 |
| 55-92276 | 7/1980 | Japan | 219/147 |
| 56-33180 | 4/1981 | Japan | 219/147 |

Primary Examiner—Wm. Carter Reynolds
Attorney, Agent, or Firm—Dority & Manning

[57] ABSTRACT

An improved automatic welder's helmet having two pneumatic cylinders to effect the closing of the helmet's dark eye lens prior to energizing the welding system for striking the welding arc, and further to maintain the dark eye lens closed until after the arc and the weldment's white afterglow have ceased. Additionally, the invention includes a ventilation system manually controlled to ventilate the helmet and to remove welding fumes and smoke from the interior of the helmet and the dark eye lens.

15 Claims, 3 Drawing Figures

AUTOMATIC WELDER'S HELMET

BACKGROUND OF THE INVENTION

This invention relates to welding helmets and the controls therefor, and specifically to welding helmets having automatically controlled dark eye shields. More particularly, this invention relates to a welder's helmet in which a dark eye shield is moved automatically into position relative to the welder's mask to protect the welder's eyes against injury from the intense flash of the welding arc. The invention includes controls that ensure that the welding system will not operate when the dark eye shield is in the opened position. The invention also includes means for cooling or ventilating the helmet interior and for defogging the dark eye shield, which is independently controllable by the operator.

There have been many attempts in the past to provide an automatic welder's helmet which will protect the operator's eyes from the intense welding arc during the welding cycle. The intense flash caused by electric arc welding, and tack welding and the like, for example is known to be injurious to the welder's eyes. The typical welder's helmet utilizes a nearly opaque or light radiation absorbing eye piece to block the intense arc light rays. In many instances, the dark eye lens is permanently affixed to the welder's helmet in such a manner that the operator must continuously manually raise and lower his helmet in order visually inspect his work. In other cases, the helmet is mounted on a head gear which permits the operator to manually flip up or slide up vertically or otherwise move the eye piece to see his work. When the welder is required to either remove the welding helmet or to manually flip up or slide up or otherwise open the eye piece, this has greatly reduced his efficiency in the welding operation. Therefore, many attempts have been made to automate the opening and closing of the dark eye shield.

One such prior art attempt is disclosed in U.S. Pat. No. 3,096,430 issued July 2, 1963 to R. S. Farr. This patent discloses a pneumatically operated eye shield which is pivotally mounted on the helmet and is opened and closed by a pneumatic cylinder. The associated electrical circuitry for controlling the welding system and the dark eye shield control unit utilizes a time delay relay in order to assure that the welding arc cannot be struck until the dark eye shield is closed. However, no provision is made in this device for assuring that the arc has completely ceased before the dark lens is opened.

A more recent attempt to provide an improved automatic welder's helmet is disclosed in U.S. Pat. No. 4,293,756 which was issued on Oct. 6, 1981 to Francis J. Niemi. The helmet disclosed in this patent is equipped with an automatic control for controlling the helmet's dark eye shield prior to energizing the electrode for striking the welding arc, and further to maintain the dark eye shield closed until after the arc and the weldment's light afterglow have ceased. The helmet also includes a ventilation system which operates to ventilate the helmet and to remove annoying welding fumes and smoke from the interior of the helmet, and especially about the eye shield itself in its lowered position on the operator's head. In one embodiment, the ventilation system operates only when the operator is using the welding system.

One major disadvantage of the helmet disclosed in the above Niemi patent is the complexity of the system for raising and lowering the dark eye shield. The dark eye shield is raised and lowered by an air cylinder which has a piston rod or shaft. This shaft is joined in the center of a yoke. The system includes a pair of guide members with appropriate guides for operation of the yoke. Such a complex system is not only expensive to manufacture, but also adds considerable weight to the helmet, which increases the fatigue of the welder using the helmet. Yet another disadvantage to the helmet of Niemi is that the ventilation system is operated automatically and does not take into consideration the individual needs of a welder. In some environments, the welder may desire more ventilation than in others, and in other environments the welder may desire to have no ventilation at all. The helmet disclosed in the Niemi patent does not permit such individual choices to be made.

Another problem is found in prior automatic welder's helmets, in that, they often allow the protective lens to be accidentally opened while the welding operation continues. Additionally, there has been the continual problem of buildup of unwanted heat and welding fumes within the welder's helmets during long periods of welding, especially when the welding is being performed on preheated fabrications. Furthermore, there is a need to protect welders who are careless and who do not properly utilize the protective helmet.

The present invention overcomes the foregoing and other problems inherent in the prior art by utilizing in the control for the welding system means to prevent commencement of welding until exhaustion of the pneumatic cylinders which automatically permits springs associated with the pneumatic cylinders to close the dark eye lens. Closing of the lens completes the circuitry for the welder. When the lens is lowered, either accidently or intentionally by the welder. As soon as the lens begins to open, the circuitry for the welding system is disconnected.

A time delay relay is preferably interposed within the circuit for actuating the mechanism for opening the dark eye lens. Consequently, the dark eye lens cannot be opened until a predetermined preset interval has expired after the circuitry for the welding system has been interrupted.

It will be seen that the automatic welder's helmet of the present invention provides protection for the welder's eyes, helps to ventilate, cool and defog the helmet's interior and lenses in accordance with the welder's desires; and increases welder productivity by eliminating welder down time. Furthermore, the present invention offers a simple and inexpensive construction, which is both lightweight and easy to use, and which due to the construction of same permits full view by the welder.

It is therefore an important object of the present invention to provide an automatic welder's helmet having a pneumatic operated dark eye shield which prevents welding when the dark eye shield is in the opened position.

It is another object of the present invention to provide an automatic welder's helmet with individually operated, manually controlled, interior ventilation means for eliminating fumes which collect in the helmet and for providing a fresh supply of air.

It is a further object of the invention to provide electrical and pneumatic control means for an automatic welder's helmet in which there is a switch means that is actuated when the dark eye lens is closed to permit the welding system becomes operable, and there is a time delay means included which is actuated when the welding system is rendered inoperable and before the dark eye lens is permitted to open.

BRIEF DESCRIPTION OF THE DRAWINGS

The means for which the foregoing and other objects of the present invention are accomplished and the manner of their accomplishment will be readily understood from the following specification and upon reference to the accompanying drawings, in which.

DESCRIPTION OF THE PREFERRED EMBODIMENT

Figure 1:
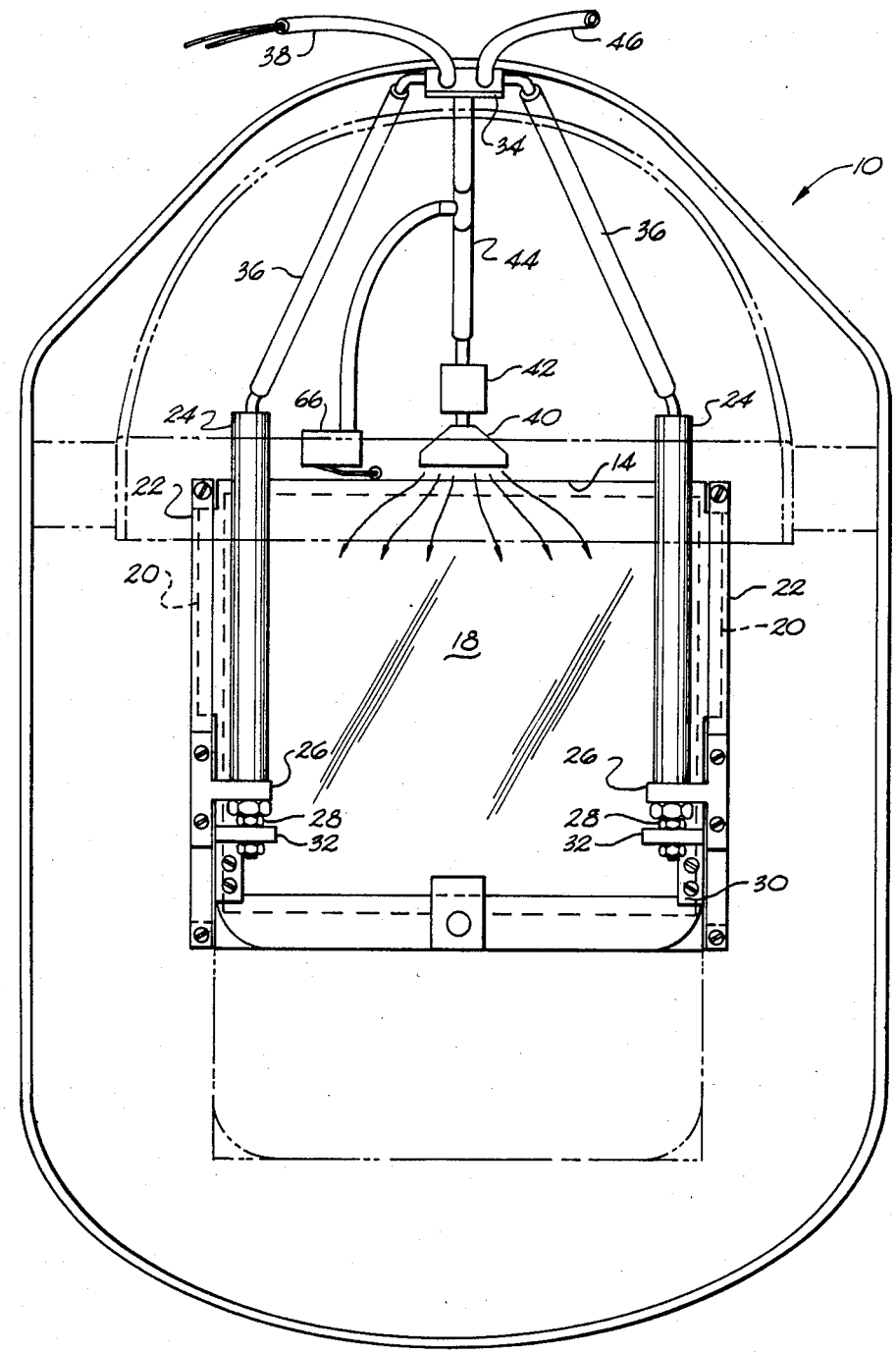
FIG. 1 is a rear elevation view of the automatic welder's helmet of the present invention, with the headgear removed for clarity and with some parts broken away.
Figure 2:
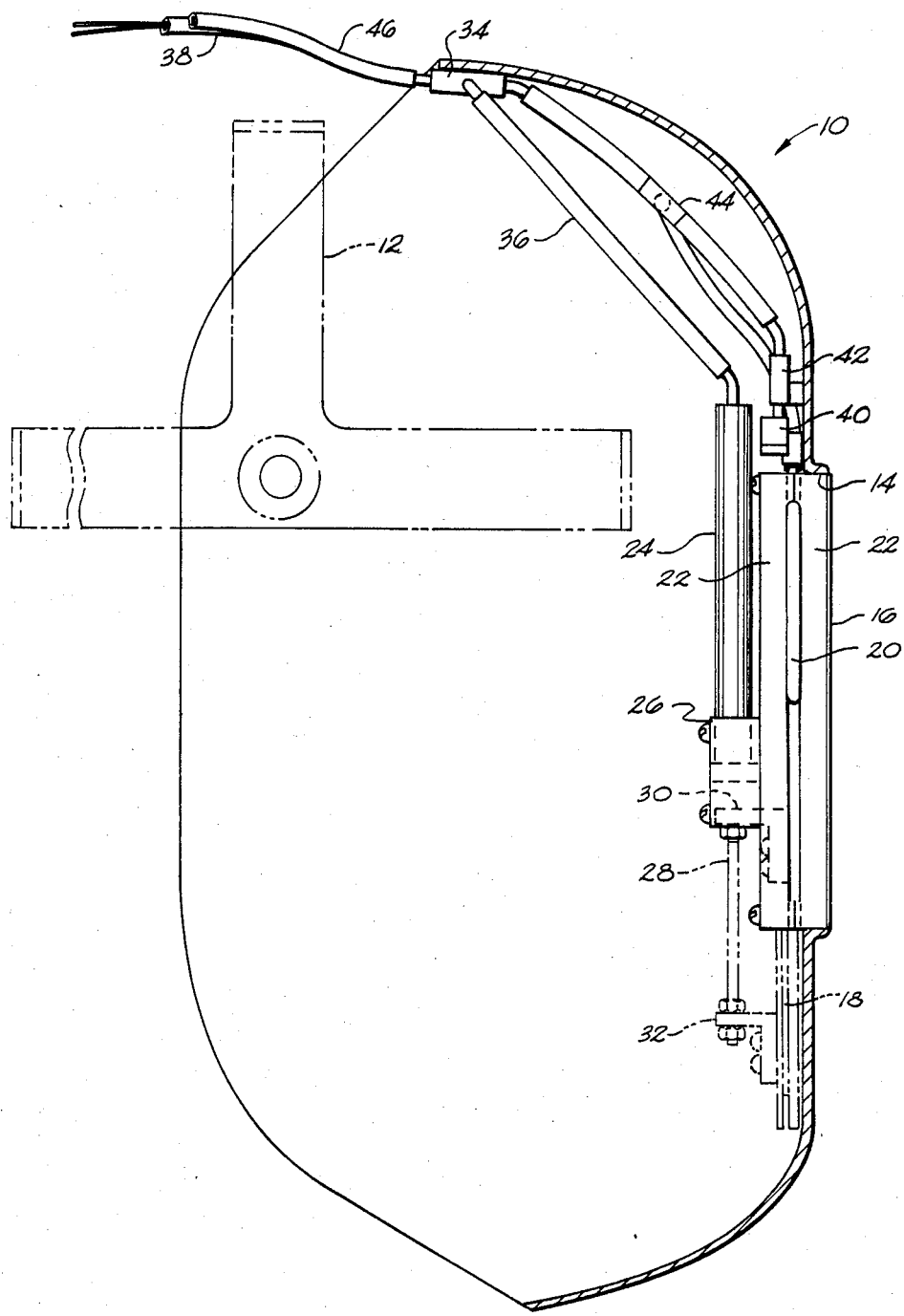
FIG. 2 is a side sectional view of the welder's helmet of FIG. 1.

Having reference to the drawings, wherein like reference numerals indicate corresponding elements of the invention, FIGS. 1 and 2 illustrate the welding helmet of the invention. The helmet of the invention comprises an open back head shield 10. Open back head shield 10 comprises the usual fiberglass hood or plastic head shield having a front planar section and a peripheral or wraparound portion. Head shield 10 is pivotally mounted to a typical head harness 12 and a construction of head shield 10 and harness is conventional.

Head shield 10 is provided with a lens opening 14 for receiving a lens frame which holds the lenses of the welding helmet. At the front of the helmet covering the lens opening 14 is a clear safety lens 16 which may be glass, plastic or another well known material. Safety lens 16 protects the welder from weld splatter and other particles which might damage the dark eye lens or injure the welder's eyes when the dark eye lens is open. On the interior surface of the open back head shield 10 is a dark eye lens 18 which is mounted in a dark eye lens frame 30. Each side of the dark eye lens frame is provided with guide tabs 20 which are guided between guide bars 22 for vertical reciprocating motion, to open and to close the dark eye lens.

Disposed on each side of the lens opening 14 is a pneumatic cylinder 24. Each of the pneumatic cylinders 24 is supported in its own support bracket 26 which is attached to the guide bars 22, and through them to the head shield 10 by means of suitable attaching devices such as rivets, screws, bolts or the like. Removable attaching devices are preferred to facilitate ease of changing of a lens as desired. Each of the pneumatic cylinders 24 includes a spring loaded piston and a piston rod 28 (see FIG. 3) which urge the piston and piston rod upwardly as seen in FIGS. 1 and 2.

Piston rod 28 is attached to the dark eye lens frame 30 by means of a piston rod connection 32. Thus, when the piston and its piston rod are urged into the upward position as seen in FIG. 1, the dark eye lens will be in the closed position.

The upper ends of pneumatic cylinders 24 are connected to air lines or hoses 36 and hoses 36 are connected to an air distributor 34 and thence to an air supply line 38. Thus, it is seen that when air is supplied to lines 36 and 38 and thence to cylinders 24, cylinders 24 will be pressurized and the pistons within the cylinder 24 will be urged downwardly within the cylinder (see FIG. 2), and will, in turn, lower the dark eye lens 18 to provide an unobstructed view for the welder. In the closed position, the welder has a full unobstructed shield view. Such full view has, in fact, not been available on prior art welding helmets which permitted only partial view due to the limited lens size and associated hardware. Whenever cylinders 24 are depressurized or the air therein is exhausted therefrom, the spring loaded pistons will return to their uppermost position and will carry with them the dark eye lens into the closed position.

Also disposed upon the interior surface of head shield 10 is an air diffuser 40 which receives clean air under pressure from nozzle 42 and diffuses it over the surface of the dark eye lens and the interior of the open back head shield. The air thus diffused defogs the dark eye lens and ventilates the head shield and removes therefrom any fumes which may have accumulated within the head shield. The clean air for diffuser 40 is supplied to nozzle 42 by means of an air hose 44 which receives the clean air from a supply line 46. As with air lines 36, hose 44 is connected to air distributor 34 which may have channels therein segregating air flow to diffuser 40 or cylinder 24, as the case may be. Also, if desired, distributor 34 could include valving means to direct air flow, or could simply be a holding bracket for the various air hose connection to air source lines 38, 46. In many cases, the air for supply lines 46 and 38 comes from a common source, but in some cases it may be desirable to supply the clean air for the diffuser from a different source than the other air for the pneumatic cylinders 24.

Figure 3:
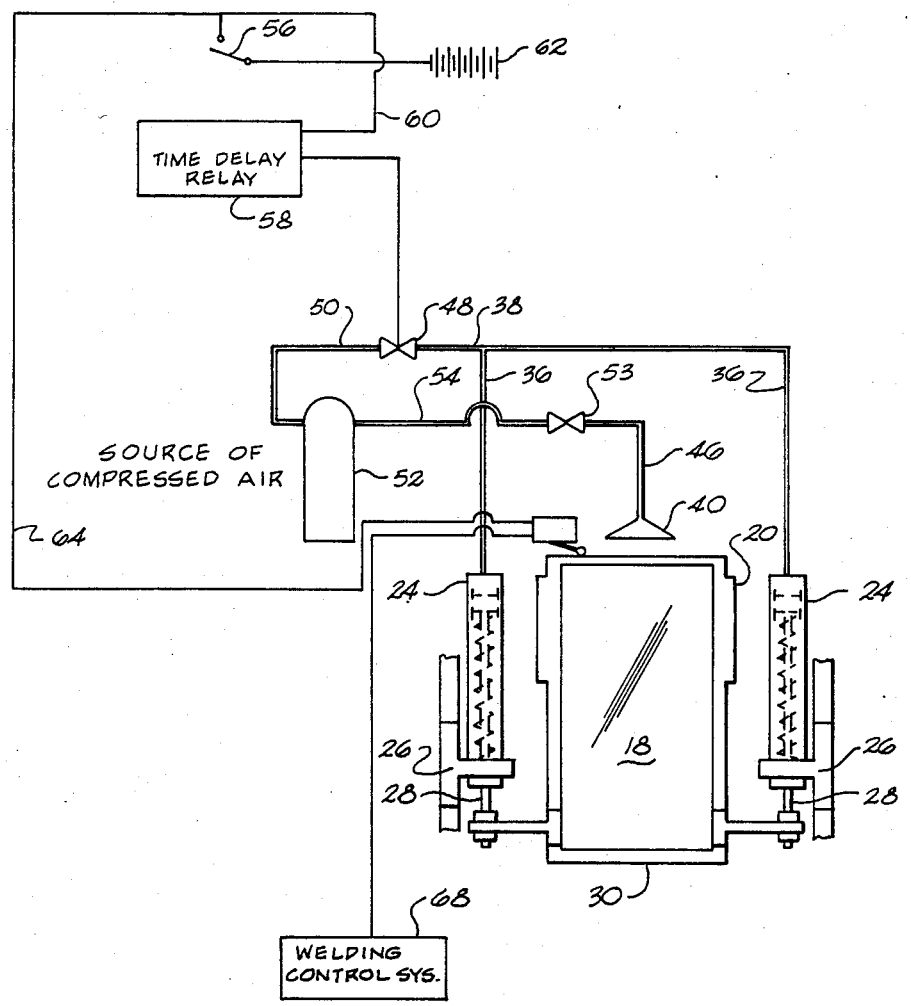
FIG. 3 is a schematic diagram depicting the electrical control circuitry used to control the welding system and the operation of the dark lens opening and closing system.

Referring now more particularly to FIG. 3, it will be noted that supply line 38 for the pneumatic cylinders is connected to a valve 48 which, in turn, is connected to a supply line 50 and therethrough to a source of compressed air 52. Valve 48 is preferably an electrically actuated solenoid valve which normally is open to the compressed air from the source 52 and to extend the cylinders 24. Whenever solenoid operated valve 48 is energized, it closes valve 48, thereby effectively disconnecting cylinders 24 to the source of compressed air 52. This, in turn, allows the springs within the cylinders 24 to close the dark eye lens.

Solenoid valve 48 is connected to a power source 62 through a time delay relay 58 (preferably adjustable) and a power line 60 and switch 56. Whenever switch 56 is closed with regard to solenoid valve line 60, solenoid valve 48 is closed and pneumatic cylinders 24 are exhausted. This, in turn, means that the dark eye lens is in the closed position because of the force exerted by the spring on the spring loaded pistons within the cylinder.

Diffuser 40 is connected to an air supply line 46, which in turn, is connected to a manually operated valve 53. Valve 53, in turn, is connected to a source of compressed air 52 by supply lines 54. Thus, it is seen, that the welder can control when, and how much, air is fed to the diffuser 40 to suit his own personal requirements.

Also, switch 56 in the closed position, connects welding supply line 64 to an electrical source 62. Power is fed through line 64 to a switch means 66, preferably a micro switch and thence to the welding control for the welding system 68. While a micro switch 66 is preferred, any switch which is actuatable by the lens in the closed portion will be adequate such as, for example, a reed switch, proximity switch, or the like. In operation, whenever switch 56 opens the operation of the welding system is disrupted and the system is at rest. When the welder has completed a particular welding task and is ready to line up his work for a second weld, he opens switch 56 to turn off or to disrupt the welding system. Power flow is disrupted from switch 56 through line 60 into time delay relay 58. After a preselected time period has passed adequate to permit cessation of residual glow, power from source 62 is disconnected by the time delay relay 58 to solenoid valve 48. Solenoid valve 48 is then opened to connect the source of compressed air 52 through lines 50 to lines 38 and 36 thereby pressurizing pneumatic cylinders 24.

As pneumatic cylinders 24 are pressurized, the pistons within the cylinders overcome the force or resistance of the springs and cause the piston rods 28 to move downwardly thereby opening the dark eye lens to provide the welder with a clear unobstructed view of the workpiece he needs to line up for his next welding job.

As noted above, as soon as switch 56 is disconnected from the contact for line 64, the welding ceases.

After the welder has lined up his new workpiece, he depresses switch 56 to commence welding on the new piece. As soon as switch 56 is closed, solenoid valve 48 closes and disconnects line 38 from source 52. At the same time, line 38 is vented to the atmosphere by solenoid valve 48 thereby exhausting the air from lines 36, 38 and pneumatic cylinders 24. Thus, the springs within pneumatic cylinders 24 cause the pistons and piston rods to move upwardly as soon as switch 56 is closed to cause the dark eye lens 18 to move to the closed position immediately.

When switch 56 is depressed by the operator to close or make contact with the line 64, the power is not transmitted immediately to the welding control system. Instead, a delay in power to the welding system is present until the dark eye lens 18 fully closes and makes contact with micro switch 66. Hence, welding system 68 cannot function until switch 66 is made which indicates a fully closed lens 18.

As can be seen in FIGS. 1 and 2, micro switch 66 is located to receive contact by lens 18 when lens 18 is in the fully closed position. Power to micro switch 66 is supplied via electrical connector 64 which passes internally of air line 44 and exits air line 44 at a coupling 45 and thence proceeds through a conduit 44' to switch 66. In this fashion, connector 64 is hidden from view within helmet 20 and also only one or more air lines thus lead from the helmet. After sufficient distance from the helmet, connector 64 will exit air line 44 through an appropriate coupling (not shown) and be connectable to a source of power.

In actual operation, switch 56 may represent the trigger switch on the electrode arm. In this case, the welder presses the switch 56 whenever he desires to perform a welding operation which will immediately exhaust the pneumatic cylinders, close the dark eye lens which makes switch 66, and permit the welding operation to begin. When the welder has completed his welding cycle, all the time having his dark lens in the fully closed position to protect his eyes, he releases the trigger switch 56 thereby immediately turning off the welding operation and operating solenoid valve 48 after the adjustable time delay relay 58 interrupts power from source 62, thereby opening the dark eye lens by pressurizing cylinders 24.

Thus, after a predetermined short delay the welder may line up his next job without having to remove his helmet or manually open the dark lens in order to see the workpieces.

As soon as the welder puts the helmet upon his head, he may adjust manual valve 53 to ventilate the helmet to his satisfaction. As the work progresses, he may adjust the flow of air through diffuser 40 as he sees fit. Normally, the air will be dispensed through diffuser 40 during the entire time that the helmet is on the head of the welder.

Switch means 66 provides a fail safe system for the helmet of the present invention. Not only will the welding system not function until the dark eye lens 18 is in the fully closed position, but also should a malfunction occur such as valve 48 permitting pressurization of cylinder 24 during welding, as soon as lens 18 moves away from switch 18, welding operation will automatically be disrupted.

From the foregoing, it is believed that those skilled in the art will readily appreciate the unique features and the advantages of the present invention over the previous types of automatic welder helmets. Further, it is to be understood that while the present invention has been described in relation to a particular preferred embodiment as set forth in the accompanying drawings, and as described herein, the same, nevertheless, is susceptible to change, variation and substitution of equivalents without departing from the spirit or the scope of the invention. It is therefore intended that the present invention be unrestricted by the foregoing description and the drawings, except as may appear in the following appended claims.

What is claimed is:

1. A welding helmet for use with an electric arc welding system, comprising:
    (a) an open back head shield;
    (b) a head harness connected to said head shield for supporting the same on the head of an operator;
    (c) a fixed clear eye lens secured in an opening in said head shield;
    (d) a movable dark eye lens mounted in a frame which is slidably secured about said opening in said head shield, said dark eye lens being operable to slide over said opening between opened and closed positions;
    (e) two pneumatic cylinders, each having a spring loaded piston and a piston rod, one of which is disposed on said head shield adjacent to each end of said dark eye lens frame, each piston rod being connected to said dark eye lens frame, the springs in said pistons urging said dark eye lens into the closed position; and
    (f) control means operatively associable with said welding system and said helmet for operating said welding system and said cylinders for depressurizing said cylinders and permitting said dark eye lens to close before the welding operation begins and for automatically pressurizing said cylinders after said welding has ceased to open said dark eye lens to permit viewing through said fixed clear eye lens during periods when the welding operation is not being performed.

2. A welding helmet as set forth in claim 1, wherein said control means for for delaying start of the welding operation until the dark eye lens is in place comprises switch means which is closed by full closure of said dark eye lens.

3. A welding helmet as set forth in claim 1, further comprising means for supplying air into the interior of said helmet to defog the dark eye lens and to cool the helmet as desired.

4. A welding helmet as set forth in claim 3, wherein said air supplying means includes valve means, independent of said control means for said welding system for controlling flow of air within said helmet as desired by one using same.

5. A welding helmet as set forth in claim 1, wherein said control means for pressurizing said pneumatic cylinders comprises a solenoid operated valve which opens to connect said pneumatic cylinders to a source of compressed air, and switch means operatively associated therewith.

6. A welding helmet as set forth in claim 5, wherein timing means is interposed in the circuit between said solenoid valve and said switch for delaying operation of said solenoid valve for a predetermined period of time after deactuation of said switch.

7. A welding helmet as set forth in claim 6, wherein said timing means is a time delay relay.

8. A welding helmet as set forth in claim 7 wherein said time delay relay is adjustable.

9. A welding helmet for use with an electric welding system, comprising:
 (a) an open back head shield;
 (b) a head harness connected to said head shield for supporting the same on the head of an operator;
 (c) a fixed clear lens secured in an opening in said head shield to permit clear vision through said head shield and at the same time to protect the operator;
 (d) a movable dark eye lens mounted in a frame, slidably secured about said opening in said head shield and operable to slide over said opening between closed and opened positions.
 (e) two pneumatic cylinders, each having a spring loaded piston and piston rod, one of which is disposed on said head shield adjacent to each end of said dark eye lens frame, said rod of each piston being connected to said dark lens frame, said springs in said pistons urging said dark eye lens towards the closed position;
 (f) an air diffuser disposed inside said head shield in a position to direct diffused air currents onto said dark eye lens of said head shield, said air diffuser being connectable to a source of air;
 (g) air distributor means connectable to a source of air and connected to one end of each of said cylinders;
 (h) control means connectable to the arc welding system for operating said cylinders to exhaust air therefrom and permit said dark eye lens to close before said welding operation begins and to pressurize said cylinders and open said dark eye lens only after said welding operation has ceased; and
 (i) manually operated valve means for supplying air to said diffuser for cooling said helmet and defogging the lens when desired.

10. A welding helmet as set forth in claim 9, wherein said control means comprises switch means which will prevent the start of the welding system until the dark eye lens is in place and makes the switch means, and timing means which will delay the pressurization of the pneumatic cylinders for opening of the dark eye lens until the welding operation has ceased.

11. A welding helmet as set forth in claim 9 wherein said air diffuser is connected to said air distributor means and said air distributor means is connectable to a common source of air for said helmet.

12. A welding helmet as set forth in claim 9 wherein said control means comprises first switch means operatively connectable with said welding system with a further switch means located operatively therebetween, and an electrically actuated solenoid valve and timing means operatively associated with said first switch means and said cylinders so that when said first switch means is operative to initiate welding, welding is permitted only after making of said further switch means when said dark eye lens is fully closed and so that when said first switch means is operative to cease welding, said timing means delays actuation of said solenoid valve and pressurization of said cylinder to open said surface lens until welding ceases.

13. A welding helmet as set forth in claim 12, wherein said timing means is at least one time delay relay.

14. A welding helmet as set forth in claim 13, wherein said at least one time delay relay is adjustable.

15. A welding helmet as set forth in claim 12 wherein said further switch means is a micro switch that is made by contact with said dark eye lens in the fully closed position.

* * * * *